United States Patent
Haines et al.

(10) Patent No.: US 6,462,822 B1
(45) Date of Patent: Oct. 8, 2002

(54) METHOD AND APPARATUS FOR DETECTING OVERHEAD TRANSPARENCIES

(75) Inventors: Robert E. Haines, Boise, ID (US); Jeffrey S. Weaver, Ft. Collins, CO (US)

(73) Assignee: Hewlett-Packard Company, Palo Alto, CA (US)

( * ) Notice: Subject to any disclaimer, the term of this patent is extended or adjusted under 35 U.S.C. 154(b) by 3 days.

(21) Appl. No.: 09/825,208

(22) Filed: Apr. 2, 2001

(51) Int. Cl.⁷ .............................................. G01N 21/47

(52) U.S. Cl. .......................... 356/446; 356/14; 356/16; 356/19; 356/101; 356/104; 356/105; 250/561; 250/559.14

(58) Field of Search ........................... 356/446; 347/14, 347/16, 19, 101, 104, 105; 250/559.14, 561

(56) References Cited

U.S. PATENT DOCUMENTS

| | | | |
|---|---|---|---|
| 4,528,054 A | 7/1985 | Stahl et al. | 156/226 |
| 4,976,993 A | 12/1990 | Sutera | 427/161 |
| 5,030,538 A | 7/1991 | Tobias et al. | 430/138 |
| 5,034,302 A | 7/1991 | Adair et al. | 430/138 |
| 5,306,686 A | 4/1994 | Patel et al. | 503/200 |
| 5,582,902 A | 12/1996 | Kanbayashi et al. | 428/206 |
| 5,709,926 A | 1/1998 | Gust | 428/206 |
| 5,875,029 A | 2/1999 | Jann et al. | 356/345 |
| 5,905,011 A | 5/1999 | Kurose et al. | 430/110 |
| 5,939,193 A | 8/1999 | Katsen et al. | 428/411.1 |
| 5,958,552 A | 9/1999 | Fukuda et al. | 428/141 |
| 5,968,667 A | 10/1999 | Assante et al. | 428/480 |

*Primary Examiner*—Bruce Anderson
*Assistant Examiner*—Zia R. Hashmi
(74) *Attorney, Agent, or Firm*—James R. McDaniel

(57) ABSTRACT

This invention relates to a method and apparatus for detecting overhead transparencies (OHT), such as a dual OHT. Dual overhead transparencies, preferably, have a coating on one side that is compatible with ink jet-type printers and a coating on the other side that is compatible with laser jet-type printers. Such structures of this type, inform the user of the type of OHT.

17 Claims, 2 Drawing Sheets

METHOD AND APPARATUS FOR DETECTING OVERHEAD TRANSPARENCIES

FIELD OF THE INVENTION

This invention relates to a method and apparatus for detecting overhead transparencies (OHT), such as a dual OHT. Dual overhead transparencies, preferably, have a coating on one side that is compatible with ink jet-type printers and a coating on the other side that is compatible with laser jet-type printers. Such structures of this type, inform the user of the type of OHT.

DESCRIPTION OF THE RELATED ART

It is known, in the transparency art, to employ an overhead transparency for color laser printers. Exemplary of such prior art is U.S. Pat. No. 5,939,193 ('193) to B. J. Katsen et al., entitled "Overhead Transparency for Color Laser Printers and Copiers." While the '193 patent discloses an overhead transparency for color laser printers and copiers, there is no teaching of a dual overhead transparency or dual OHT. Also, the '193 patent does not disclose a method for detecting the proper side of an OHT.

It is also known, in the transparency art, to employ a dual OHT. Exemplary of such prior art is U.S. Pat. No. 5,030,538 ('538) to R. H. Tobias et al., entitled "Method for Producing Overhead Transparencies Having High Color Density Images Using a Double-Sided Image Recording Material." While the '538 reference addresses the deficiencies of the '193 patent with respect to the use of a dual OHT, the '538 reference also fails to disclose a method for detecting the proper side of the OHT.

It is apparent from the above that there exists a need in the art for a detection system which is a lightweight through simplicity of parts and uniqueness of structure and which is capable of detecting the proper side of an OHT. It is a purpose of this invention to fulfill this and other needs in the art in a manner more apparent to the skilled artisan once given the following disclosure.

SUMMARY OF THE INVENTION

Generally speaking, this invention fulfills these needs by providing a method for detecting overhead transparencies, comprising the steps of: placing at least one overhead transparency having a first composition into a media tray of the printer; composing a document to be printed; sensing the transparency to determine if the transparency can be printed upon by the printer; placing, if necessary, a transparency having a second composition in the media tray; and printing the document on the transparency having either the first or second composition.

In certain preferred embodiments, the overhead transparency (OHT) can be, but is not limited to, a dual purpose OHT or other suitable print media. Also, the OHT is sensed by a specular and diffuse sensing system. Also, the method includes the step of flipping the OHT so that the proper side of the OHT can be printed upon. Finally, the method includes the step of determining if the OHT is properly oriented.

In another further preferred embodiment, various types of overhead transparencies or other types of media, whether or not the transparencies are dual overhead transparencies, can be detected and the user informed of the transparency available for printing.

The preferred system, according to this invention, offers the following advantages: lightness in weight; ease of assembly and repair; good stability; good durability; excellent economy; and excellent transparency measurement characteristics. In fact, in many of the preferred embodiments, these factors of economy and transparency measurement characteristics are optimized to an extent that is considerably higher than heretofore achieved in prior, known transparency measurement systems.

The above and other features of the present invention, which will become more apparent as a description proceeds, are best understood by considering following detailed description in conjunction with the accompanying drawings, wherein like characters represent like parts throughout the several views and in which:

DETAILED DESCRIPTION OF THE INVENTION

Transparencies for use in ink jet-type printers have a special ink retention coating to absorb ink. This retention coating is not compatible with a laser jet-type printer. Typically, if an ink jet-type transparency is used by a laser jet-type printer, the ink jet-type transparency will adhere to the fuser of the laser jet-type printer and adversely affect the printing characteristics of the laser jet-type printer.

Figure 1:
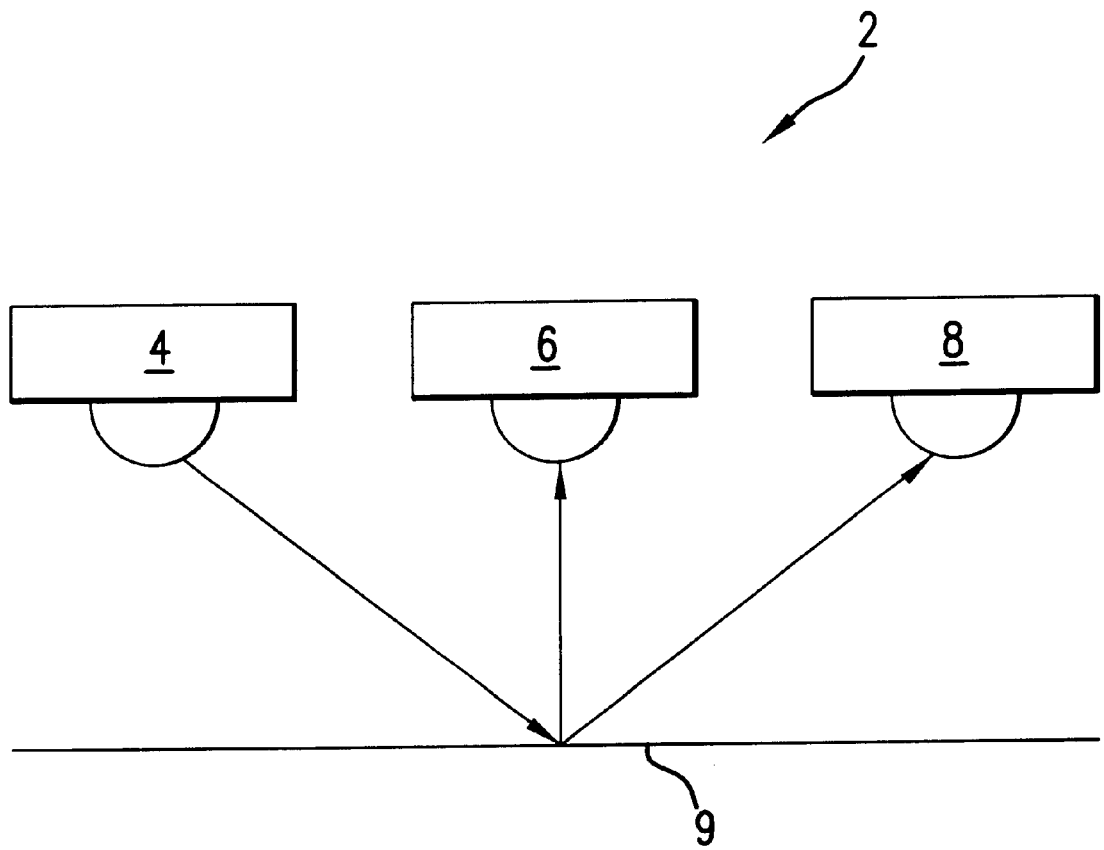
FIG. 1 is a schematic illustration of a specular and diffuse sensing system, according to one embodiment of the present invention.

With reference first to FIG. 1, there is illustrated one preferred embodiment for use of the concepts of this invention. FIG. 1 illustrates a specular and diffuse sensing system 2. System 2 includes, in part, light source 4, diffuse sensor 6, specular sensor 8, and media 9. An example of a device for surface inspection by specular and diffuse light detection can be found in U.S. Pat. No. 5,875,029 ('029) to P. C. Jann et al., entitled "Apparatus and Method for Surface Inspection by Specular Interferometric and Diffuse Light Detection." As described in the '029 reference, diffuse sensor 6 and specular sensor 8 use two forms of a light reflected from media 9 to characterize properties of media 9. The first form of reflected light is specularly reflected from smooth regions of media 9 and detected by specular sensor 8. Light source 4 shines an incident beam of light at media 9. The angle of specular reflectance is equal to the angle of incidence from the light source 4. If the media has a perfectly smooth finish (a mirror), all of the incident light from source 4 will be reflected at an angle equal to the angle of incidence into detector 8. If the surface of media 9 is not smooth this will impart a scattering of light at an angle different than the angle of incidence from the source thereby reducing the intensity of the light received by detector 8. Other media properties such as color, light composition or refraction may also impact the light received by detector 8. System 2 also uses diffusely-related light to sense roughness of media 9 which scatters incident light from the surface of media 9. This diffusely-scattered light is detected by diffuse sensor 6. Sensor 6 is located at a position other than a point where the angle of reflectance is equal to the angle of incidence. It is understood that sensor 8 does not have to be located exactly where the angle of reflectance equals the angle of incidence—this is merely the preferred position.

It is to be understood that other types of sensing systems could be utilized to detect media 9. For example, a CCD array could be employed which continuously measures media 9 in order to get a continuous "signature response" from media 9 that is indicative of that particular type of media 9. The CCD array replaces sensors 6 and 8 and measures a continuous range of angles between the location of sensor 6 and sensor 8. In this manner, the printer can more easily manipulate media 9 in order to print on the proper side of media 9. It is also to be understood that media 9 can be any type of media that is capable of being printed upon.

Figure 2:
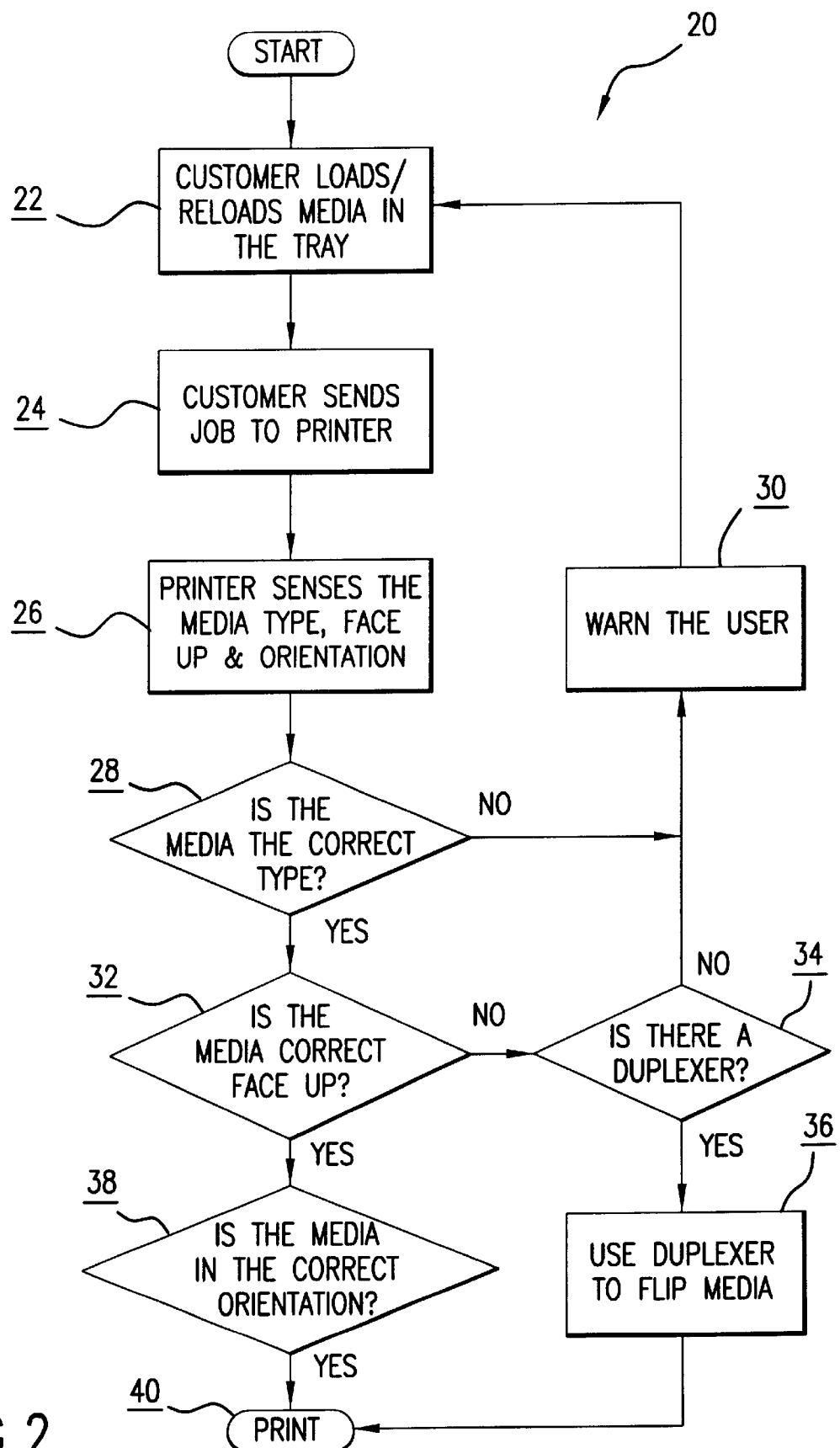
FIG. 2 is a flowchart representing a method for detecting different types of overhead transparencies, according to one embodiment of the present invention.

With respect to FIG. 2, method 20 for detecting the type of media/OHT will now be described. First, the user/customer loads/reloads media/overhead transparencies into a tray of the printer (not shown), as shown in step 22. The user composes a document on a personal computer, for example, and sends the document to be printed on the media/OHT by the printer, as shown in step 24. The printer senses the type of media/OHT available in the printer tray through system 2, as shown in step 26. It is also to be understood that system 2 can also sense whether or not the proper side of the media/OHT is facing up and whether or not the media/OHT is properly oriented based upon the location of media 9 with respect to system 2. System 2 responds back to the user through the printer to inform the user if the media type in the tray of the printer is the correct media type, as shown in step 28. If the media type is not the correct media type, system 2 and the printer will warn the user through a conventional user interface (not shown) located on the printer, as shown in step 30. In the case where the media type is incorrect, the user merely has to place the proper media type into the printer tray. For example, if an ink jet-type OHT is located in the paper tray of a laser jet-type printer, the ink jet-type OHT may stick to the fuser of the laser jet-type printer and adversely affect the operating characteristics of the laser jet-type printer, as previously discussed.

System 2 can determine if media 9 is facing in the proper direction based upon the location of media 9 with respect to system 2, as shown in step 32. For example, if the user has loaded a dual purpose OHT into the paper tray of the printer and the user is employing a laser jet-type printer, system 2 will determine from the presence or absence of media 9 if the laser jet-type side of the dual purpose OHT is facing in the proper direction. The printer will conventionally inform the user if the printer has duplexing capabilities, as shown in step 34. If the ink jet-type side of the dual purpose OHT is facing up, as evidenced by the presence or absence of media 9, then the printer will employ a conventional duplexer to flip the dual purpose OHT so that the laser jet-type side of the dual purpose OHT is facing up so that it can be printed on by the laser jet-type printer, as shown in step 36.

System 2 can also determine if media 9 is oriented in the proper direction by the location of media 9 with respect to system 2, as shown in step 38. If media 9 is properly oriented, the printer will then conventionally print the document on the OHT, as shown in step 40.

Once in the above disclosure, many other features, modifications or improvements will become apparent to the skilled artisan. Such features, modifications or improvements are, therefore, considered to be a part of this invention, the scope of which is to be determined by the following claims.

What is claimed is:

1. A method for detecting overhead transparencies, wherein said method is comprised of the steps of:

placing at least one overhead transparency having a first composition into a media tray of the printer;

composing a document to be printed;

sensing said transparency to determine if said transparency can be printed upon by said printer;

placing, if necessary, a transparency having a second composition into said media tray; and printing said document on said transparency having either said first or second composition.

2. The method, as in claim 1, wherein said overhead transparency is further comprised of:

a dual purpose overhead transparency.

3. The method, as in claim 1, wherein said sensing step is further comprised of the steps of:

sensing a specular reflection from said overhead transparency; and sensing a diffuse reflection from said overhead transparency.

4. The method, as in claim 1, wherein said method is further comprised of the step of:

determining if a correct side of said transparency is facing up.

5. The method, as in claim 4, wherein said determining step is further comprised of the steps of:

flipping said transparency to get the correct side to face up; and determining if said correct side of said transparency is facing up.

6. The method, as in claim 1, wherein said method is further comprised of the step of:

determining if said transparency is properly oriented.

7. A method for detecting media type, wherein said method is comprised of the steps of:

placing at least one sheet of media having a first composition into a media tray of the printer;

composing a document to be printed;

sensing said media to determine if said media can be printed upon by said printer;

placing, if necessary, a media having a second composition into said media tray; and printing said document on said media having either said first or second composition.

8. The method, as in claim 7, wherein said media is further comprised of:

an overhead transparency.

9. The method, as in claim 8, wherein said transparency is further comprised of:

a dual purpose overhead transparency.

10. The method, as in claim 7, wherein said sensing step is further comprised of the steps of:

sensing a specular reflection from said media; and sensing a diffuse reflection from said media.

11. The method, as in claim 7, wherein said method is further comprised of the step of:

determining if a correct side of said media is facing up.

12. The method, as in claim 11, wherein said determining step is further comprised of the steps of:

flipping said media to get the correct side to face up; and determining if said correct side of said media is facing up.

13. The method, as in claim 7, wherein said method is further comprised of the step of:

determining if said media is properly oriented.

14. The method, as in claim 1, wherein said sensing step is further comprised of the step of:

measuring a signature response of said transparency.

15. A method for detecting media type, wherein said method is comprised of the steps of:

placing at least one sheet of media having a first composition into a media tray of the printer;

composing a document to be printed;

sensing said media to determine if said media can be printed upon by said printer;

placing, if necessary, a media having a second composition into said media tray; and printing said document on said media having either said first or second composition.

16. The method, as in claim 15, wherein said sensing step is further comprised of the steps of:

sensing a specular reflection from said media; and sensing a diffuse reflection from said media.

17. The method, as in claim 15, wherein said sensing step is further comprised of the step of:

measuring a signature response of said media.

* * * * *